(12) United States Patent
Sander (10) Patent No.: US 7,724,429 B2
(45) Date of Patent: May 25, 2010

(54) MICROSCOPE HAVING A SURGICAL SLIT LAMP HAVING A LASER LIGHT SOURCE

(75) Inventor: Ulrich Sander, Rebstein (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 227 days.

(21) Appl. No.: 11/459,344

(22) Filed: Jul. 22, 2006

(65) Prior Publication Data

US 2007/0024965 A1 Feb. 1, 2007

(30) Foreign Application Priority Data

Jul. 26, 2005 (DE) .................. 10 2005 034 829

(51) Int. Cl.
*G02B 21/06* (2006.01)
(52) U.S. Cl. ...................... 359/390; 359/385
(58) Field of Classification Search ................. 359/385, 359/390
See application file for complete search history.

(56) References Cited

U.S. PATENT DOCUMENTS

2002/0151784 A1* 10/2002 Mizoguchi et al. .......... 600/407
2005/0079603 A1* 4/2005 Sandstrom ............... 435/288.7
2005/0195360 A1* 9/2005 Akita et al. .................. 351/212
2005/0240168 A1* 10/2005 Neuberger et al. ............. 606/4

FOREIGN PATENT DOCUMENTS

DE          42 27 942 C2     3/1993

OTHER PUBLICATIONS

Leica Microsystems; Ophthalmo-logic Accessories for Ophthalmology; Leica Slit Illuminator for M841; Selling Guide OPH; Update (Jul. 2002); p. 10.5.
Wernicke, et al.; The Digital-Optical Laser System—A New Generation of Optical Components; Presentation at Laser 2003; Humboldt-Spektrum (Jan. 2003); pp. 54-57.
Leica Microsystems; Operation Gap Light H for Zeiss Operating Microscopes 1,6S and 6C Product Information; (1982); 2 pages.

\* cited by examiner

*Primary Examiner*—Joshua L Pritchett
(74) *Attorney, Agent, or Firm*—Hodgson Russ LLP (57) ABSTRACT

The invention relates to a microscope (10) having an illumination apparatus (26) having a light source (1) and an optical system. The light source (1) is embodied to output a coherent light beam bundle along a defined illumination beam path (2a), and the optical system in the illumination beam path (2a) encompasses a spatial light modulator (3) for modifying the illuminated field (4). A surgical microscope (10) is preferably equipped with an illumination apparatus (26) of this kind that is arranged adjustably in two directions on the surgical microscope (10).

23 Claims, 6 Drawing Sheets

MICROSCOPE HAVING A SURGICAL SLIT LAMP HAVING A LASER LIGHT SOURCE

CROSS REFERENCE TO RELATED APPLICATIONS

This application claims priority of the German patent application no. 10 2005 034 829.7 filed Jul. 26, 2005, which is incorporated by reference herein.

FIELD OF THE INVENTION

The invention relates to a microscope having a slit lamp that is used in ophthalmology for surgery and diagnosis.

BACKGROUND OF THE INVENTION

A slit lamp is generally understood to be an illumination apparatus that is used to view the front portion of the eye (lens and proximal vitreous body, and for inspection when fitting contact lenses). With the aid of the slit image, structures and layers in the eye can be better recognized during diagnostic and surgical procedures. Surgical slit lamps are used for the most part in combination with a surgical microscope in intraocular and especially in retinal surgery. By means of the rectangular illuminated field on the retina, membranes that have become diseased, which are very thin but nevertheless greatly reduce the patient's sight, can be detected early and successfully operated on.

Surgical slit lamps of this kind are on the market, for example, under the name "Leica Slit Illuminator," and are described in Leica Selling Guide OPH 07/02, page 10.5.

The lamp housings of these surgical slit lamps are very bulky, however, because of the light source incorporated thereinto, which is usually a halogen lamp. In addition, such known surgical slit lamps contain not only the light source but also the imaging optics and the aperture that generates the slit. Efforts have been made to minimize the size of surgical lamps by at least replacing the halogen lamp with a fiber-optic light supply system (e.g. DE-C2-4227942).

The obligatory mounting location for surgical slit lamps is below the main objective of a surgical microscope. Bulky structures at this mounting location are undesirable, however, because they reduce the open working distance and are thus disadvantageous for the overall handling of the surgical microscope.

SUMMARY OF THE INVENTION

It is the object of the invention to create a surgical slit lamp that eliminates as effectively as possible the indicated disadvantages of surgical slit lamps of the existing art.

The inventor has recognized that with the use of new optical elements, the bulky structure of the conventionally used imaging optical elements can be avoided.

In an article in Humboldt-Spektrum 1/2003, pp. 54 ff., the authors (Günther Wernicke, Sven Krüger, Marcel Rogalla, and Stephan Teiwes) present, under the title "The digital-optical laser system—a new generation of optical components," this new technology, the knowledge gained from it, and the present state of development. This technology preferably involves microdisplays that can influence light-wave fronts in amplitude and/or phase in high-resolution fashion. They can be used as switchable optical components, in the form of lenses, prisms, gratings, or even holograms. Light modulator systems of this kind (so-called "spatial light modulators" or SLMs) can be utilized, for example, as an objective having a variable focal length, as a grating having a switchable diffraction angle, as a prism, and especially as a diffractive beam splitter and beam shaper. Particularly worthy of attention in this new technology are, in particular, the addressing and modulating properties that can be achieved with new optical microdisplays based on liquid crystal on silicon (LCOS) in combination with the control of laser light.

The inventor has recognized that a novel surgical slit lamp having a decreased volume along with improved properties can be created with the use of a light modulator.

For this, the conventional light source (incandescent bulb, halogen lamp) is in some circumstances replaced by a laser that, for illumination of the retina, preferably emits red light. The collimated light beam of the laser strikes the light modulator, which can be a diffractive optical element, a hologram, or a switchable optical element of the kind described above. A "switchable optical element" is to be understood in particular as a microdisplay.

A preferred variant embodiment of a surgical slit lamp made up of the above-described components encompasses a light source, e.g. a laser, that selectively emits the desired wavelengths of red, green, and blue. It is also possible to generate white light by combining different lasers of various wavelengths. Also conceivable, however, are lasers that emit white light from the outset.

An advantage is that because of the laser that can be used, the spectral light distribution of a slit lamp in the configuration described can be adapted in almost any desired fashion.

It is possible with the light modulator system according to the present invention, depending on the design of the system, to depict specific illuminated-field shapes, e.g. a slit or a ring pattern, or also structures and images that vary over time, which are generated by an electronics unit in conjunction with a computer. Elements that image optically (refractively) in the conventional sense are essentially no longer necessary.

A further advantage of a slit lamp according to the present invention is the size that is now achieved: approximately that of a pack of cigarettes. Conventional slit lamps of the existing art usually have a volume corresponding approximately to that of the microscope (approx. 100×200×200 mm).

Further variant embodiments that are a possibility are slit lamps according to the present invention equipped with light modulators that, by means of predetermined fixed patterns, "modulate" the light striking them.

The light modulators can simultaneously also be configured as mirrors or as reflective displays, which are then arranged as a deflecting mirror that reflects the illumination in.

As already mentioned above, provision is made for generating by means of the light modulator, for example, a slit or a ring or even a crescent as the illumination. A rectangular illuminated field is particularly suitable for detecting membranes in the eye, and offers a view with a good perception of depth. A crescent-shaped illuminated field, on the other hand, can be particularly suitable for reflection-free illumination. With the crescent shape, it is possible to prevent illumination of the patient's iris or of the entire surrounding area, which generates undesirable reflections.

A further exemplifying embodiment of the present invention provides, however, for the light modulator to deflect the laser beam so as to produce in the object a central, e.g. preferably round illuminated field, with which the so-called red reflection can be generated in improved fashion. The advantage of this deflection is that the light beam generating the illuminated field passes through the pupil of the patient's eye. The result is that no surrounding-area illumination, which might disturb the surgeon in terms of perceiving the illuminated field in the interior of the patient's eye, can be produced. In this case as well, a laser diode having a red wavelength is preferred. The advantage of this manner of generating the red reflection is that only harmless red light is used, so there is no so-called blue light hazard or UV light or IR light.

Provision is furthermore made for the mechanical coupling of the slit lamp onto the surgical microscope to be adjustable. Known for this purpose are circular-arc-segment carriers that allow a pivoting motion of the illumination system from a location angularly offset with respect to the microscope's axis, through a central coaxial location, into a location angularly offset in the opposite direction. As this pivoting motion is carried out, the slit-shaped illuminated field can be arranged, for example, perpendicular to or also parallel to the pivoting direction. Also conceivable, however, is an embodiment which offers (in a manner similar to the phases of the moon) a crescent-shaped illuminated field in the outermost pivot position, which transitions into a rectangular or square illuminated field at the central position and then assumes a mirror-reversed crescent shape on the other side of the central location.

The above-described circular-arc-segment carrier ensures a lateral adjusting motion of the slit lamp extending transversely to the surgeon's position. In order to achieve optimum illumination of the patient's eye, however, a longitudinal displacement of the slit lamp, with or without the circular-arc-segment carrier, can also prove to be a useful adjustment capability. This is the case in particular in terms of an optimum red reflection having the highest possible contrast; this depends not necessarily only on very bright illumination, but also on the particular incidence angles governed by the situation.

In addition to the adjustment motions described above, a rotation of the slit lamp about its own axis can preferably also be provided for.

A further preferred variant embodiment of a microscope having an illumination apparatus according to the present invention provides for the illumination apparatus to be removable. This makes it possible selectably to effect illumination with a modulated (modified) light-beam bundle, or instead to provide an (additional) conventional microscope illumination system at that mounting location.

Within the scope of the invention, the light modulator can certainly be embodied to generate a predetermined shape of the light-beam bundle, i.e., for example, to generate slit light, ring light, or also a central illuminated field. It is preferred, however, if the light modulator is controllable by way of an electronic control unit coupled to it, so that structures varying over time can be generated, for example with the aid of a computer or another control unit. With computer-assisted control of the light modulator, the shape and size (height, width) of the illuminated field can be varied. This control of the light modulator also offers the possibility of switching in freely selectable fashion back and forth between different aforesaid illuminated-field shapes.

The embodiments according to the present invention of a surgical slit lamp are presented below in combination with a microscope. They can also be utilized, however, in a so-called diagnostic slit lamp that is in principle also made up of a slit lamp and a magnifying observation apparatus.

Further embodiments of the invention are described in the Figures and in the dependent Claims. The Parts List is also a constituent of the disclosure.

BRIEF DESCRIPTION OF THE DRAWINGS

The invention will now be explained further, symbolically and by way of example, with reference to Figures.

The Figures are described in continuously and overlapping fashion. Identical reference characters denote identical components; reference characters having different indices indicate functionally identical or similar components.

In the Figures.

DETAILED DESCRIPTION OF THE INVENTION

Figures 1, 1A:
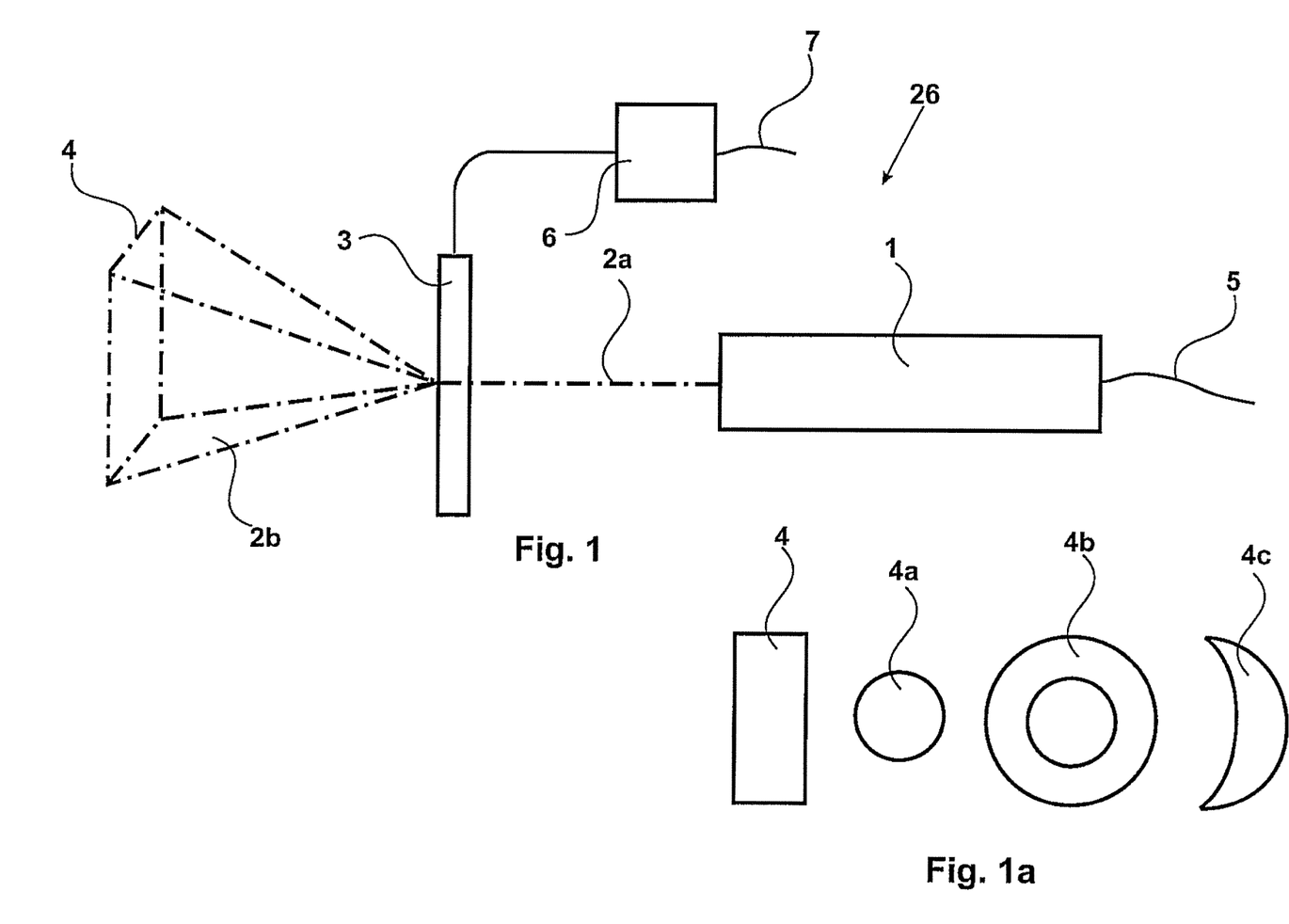
FIG. 1 is a diagram of a first embodiment according to the present invention of an illumination apparatus.
FIG. 1a shows possible shapes of illuminated fields.

FIG. 1 schematically depicts an illumination apparatus 26 according to the present invention in which a conventional light source, such as an incandescent bulb, a halogen lamp, or the like, is replaced by a light source for the output of coherent light. In a preferred embodiment, this light source for coherent light is a laser diode 1 that is powered from an electrical energy source (not depicted) via an electrical supply lead 5.

The wavelength of this laser diode 1 can be selected in accordance with requirements, but there are also laser diodes that can be excited to output laser light of selectably different wavelengths. For retinal surgery, it will be preferable to select a laser diode 1 that emits red light. It should be mentioned that many laser diodes do not emit entirely coherent light; but a light of this kind is still to be regarded, in the context of the present description, as being embraced by the term "coherent." In addition, the output of laser diode 1 can be adapted to particular requirements depending on the application.

The illuminating beam emitted by laser diode 1, which beam is symbolically depicted by its axis 2a, strikes a spatial light modulator 3.

Associated with spatial light modulator 3 is a control unit 6 that is connected via a supply lead 7 to a power source. The illuminated fields depicted in FIG. 1a—rectangle (slit) 4, round illuminated field 4a, annular illuminated field 4b, or crescent-shaped illuminated field 4c—can be formed by way of the influence exerted by control unit 6 on spatial light modulator 3. Control unit 6 is capable of varying the size of the illuminated fields and causing them to appear automatically in chronological sequence, and permits a switchover from one specific illuminated-field shape to another. This switchover preferably occurs as a continuous transition from one illuminated-field shape to the other.

Figure 1B:
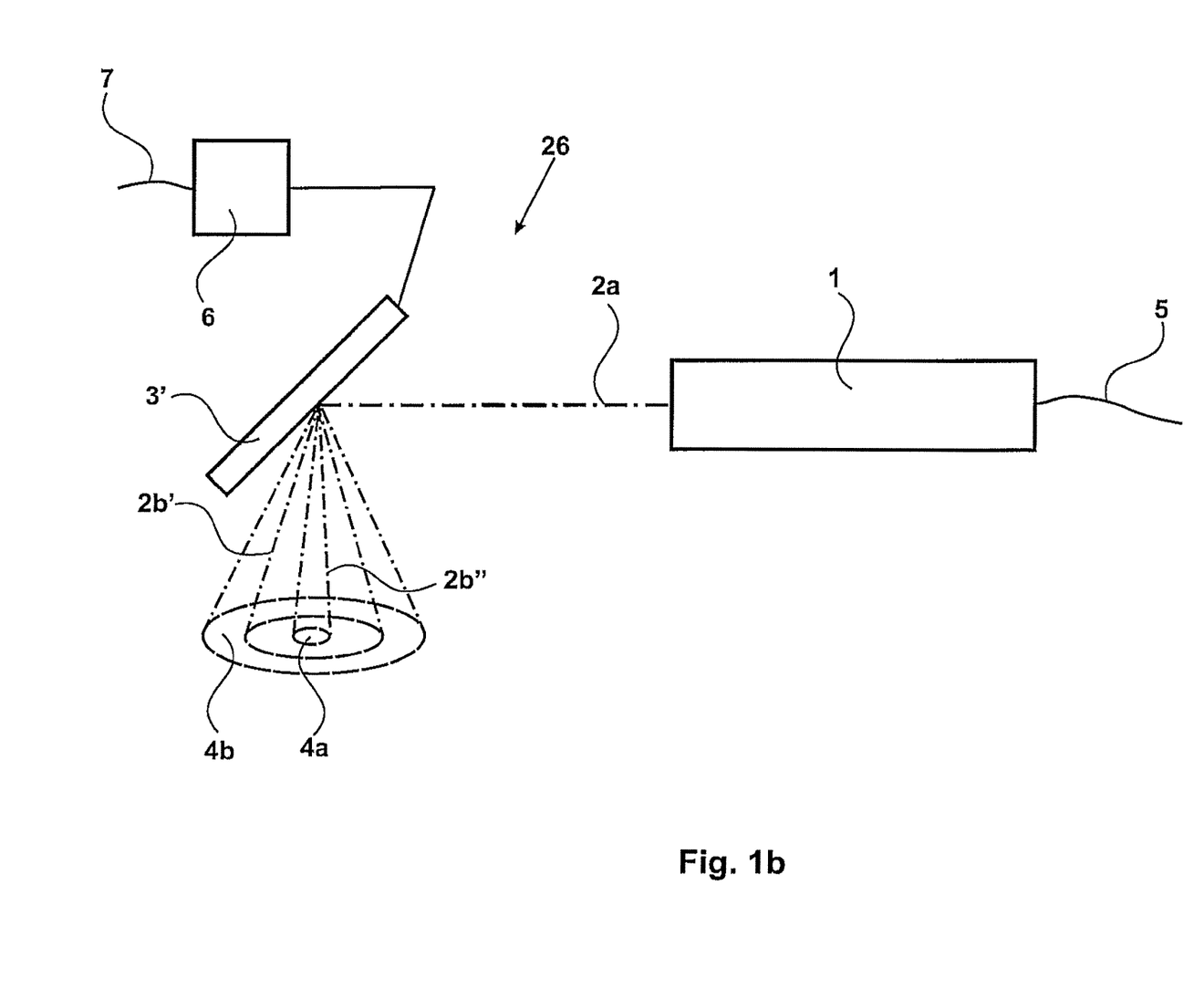
FIG. 1b shows an embodiment according to the present invention corresponding to FIG. 1, but having a spatial light modulator that is arranged as a deflecting mirror.

FIG. 1b shows a slightly modified variant embodiment of an illumination apparatus 26 according to the present invention, in which a spatial light modulator 3' is configured and arranged as a deflecting mirror. This Figure depicts, by way of example, the manner in which spatial light modulator 3' furnishes an illumination that is made up of a central illuminated field 4a and an illumination ring 4b.

Figure 2:
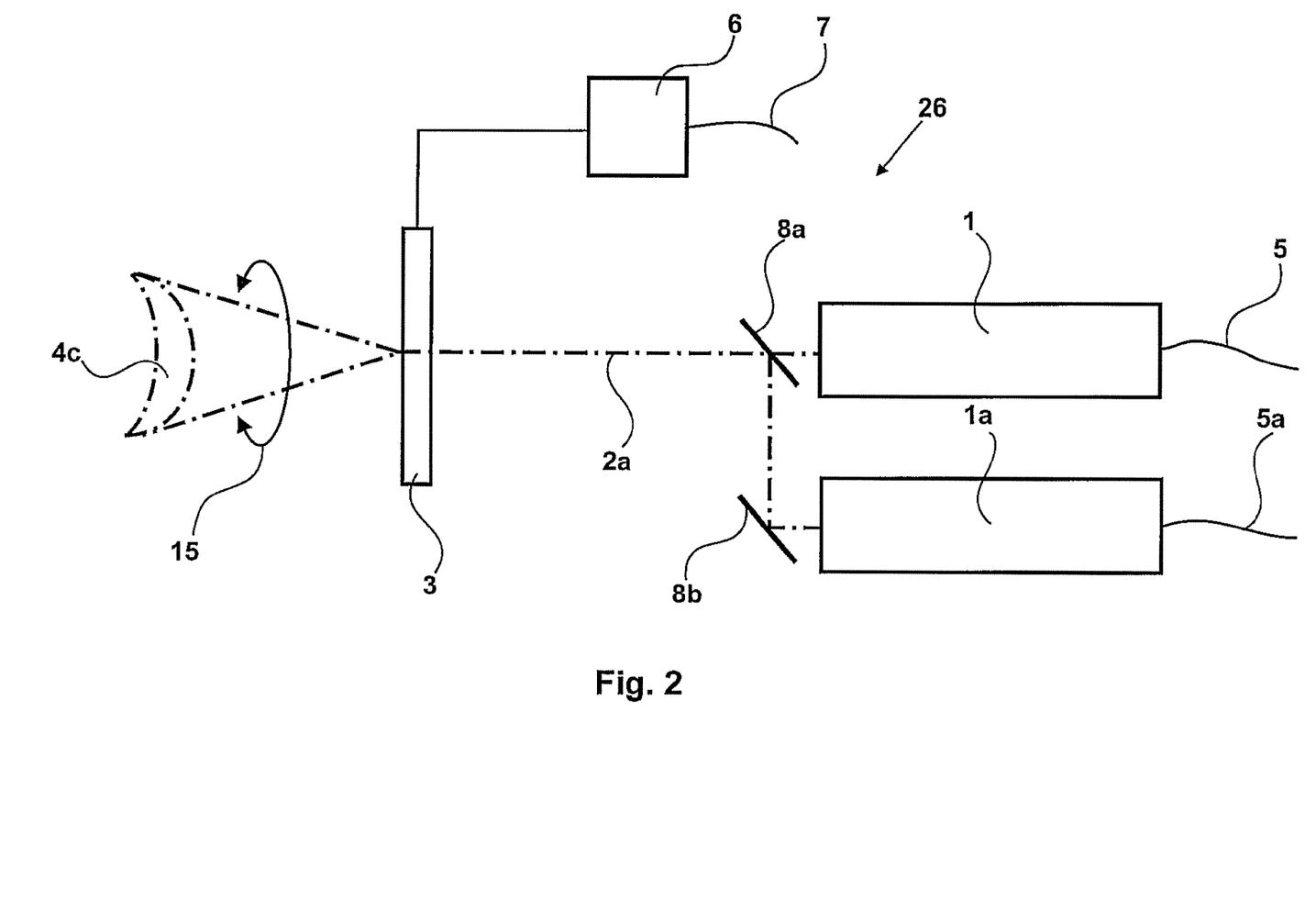
FIG. 2 is a diagram of a second embodiment according to the present invention of an illumination apparatus having two laser diodes.

FIG. 2 shows an arrangement having two laser diodes 1 and 1a, although this is to be regarded only as example since, for example, more than two laser diodes can also be utilized. It is preferred if laser diode 1a (by the arrangement of a deflecting mirror 8b or a deflecting prism), and laser diode 1 (by the arrangement of a semitransparent mirror 8a aligned parallel thereto) are reflected coaxially into the illumination beam path, which is depicted symbolically by way of its axis 2a.

With an arrangement of this kind it is possible to use laser diodes 1, 1a having different wavelengths, in order either to selectively direct one or the other wavelength (e.g. red, green, blue, etc.) onto the object, or to generate white light by mixing the corresponding wavelengths. It is clear in this context that the use of multiple laser diodes 1, 1a of approximately the same emitted wavelength can also be employed in order to increase the light intensity.

In the present variant embodiment, spatial light modulator 3 is designed to generate a crescent-shaped illuminated field 4c. A rotation of illumination apparatus 26 about axis 2a of the illumination beam path can also cause crescent-shaped illuminated field 4c to describe a rotational motion 15 in any desired fashion. This can occur manually or in electrically motorized fashion, but spatial light modulator 3 can likewise be excited electronically, solely by the influence of controller 6, in order to rotate crescent-shaped illuminated field 4c.

Figure 3:
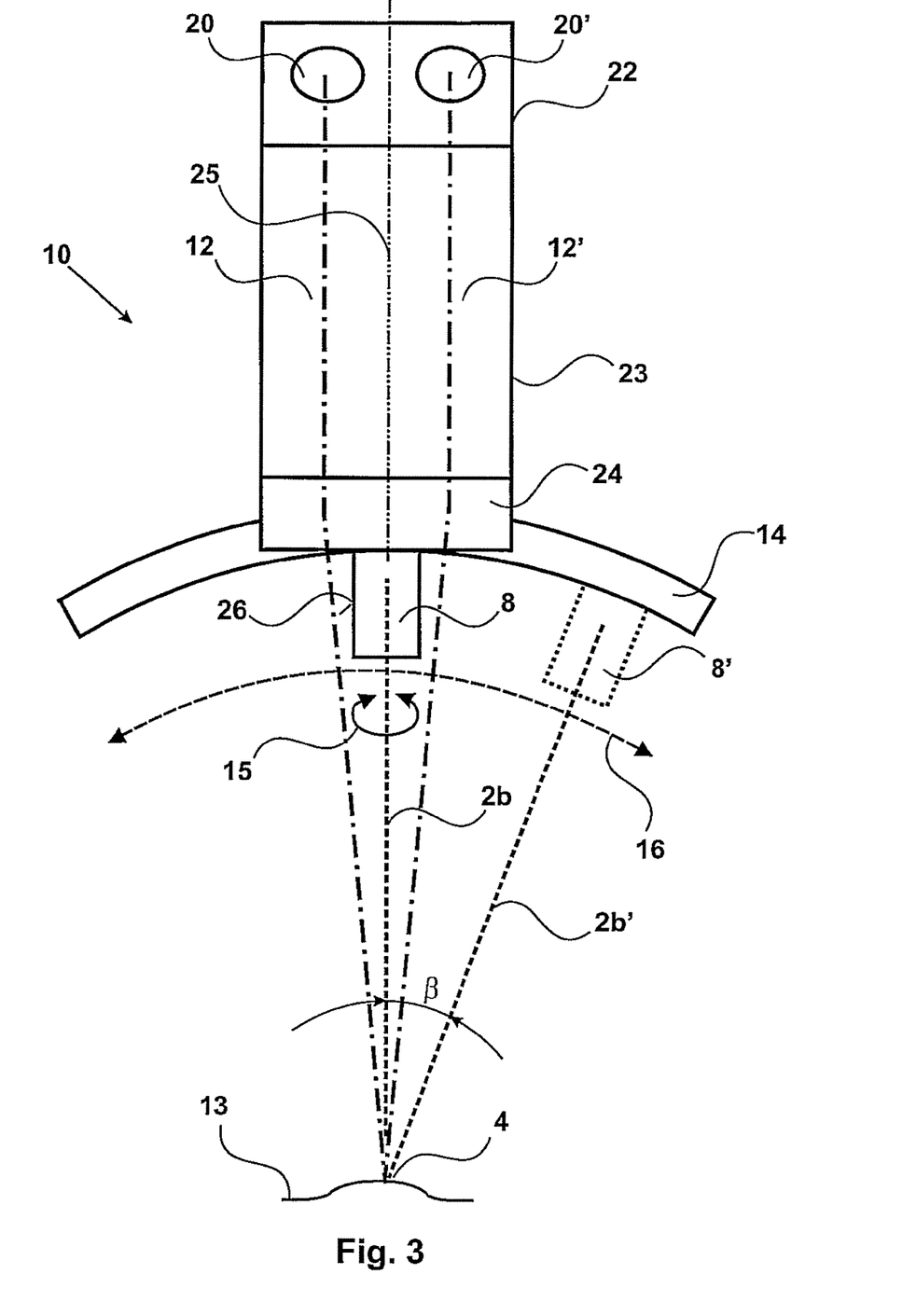
FIG. 3 is a front view of a microscope having an embodiment according to the present invention of an illumination apparatus.

FIG. 3 is a front view of a microscope 10 having an illumination apparatus 26 according to the present invention. The symbolically depicted light beams coming from object 13 are received by main objective 24 and conveyed through microscope housing 23 and tube housing 22, via two beam paths having axes 12 and 12', to eyepieces 20 and 20'. Arranged on the back side of microscope housing 23 is a circular-arc-segment carrier 14 that permits a pivoting motion 16 of illumination apparatus 26. This pivoting motion 16 can occur manually or in electrically motorized fashion. All that is visible of the illumination apparatus in this front view is deflecting prism 8, which is depicted in a central pivot position, corresponding to microscope axis 25, on circular-arc-segment carrier 14. When illumination apparatus 26 is pivoted into position 8', the modulated illumination beam path, which is depicted symbolically by way of its axis 2b', encloses an illumination incidence angle β with microscope axis 25.

Figure 3A:
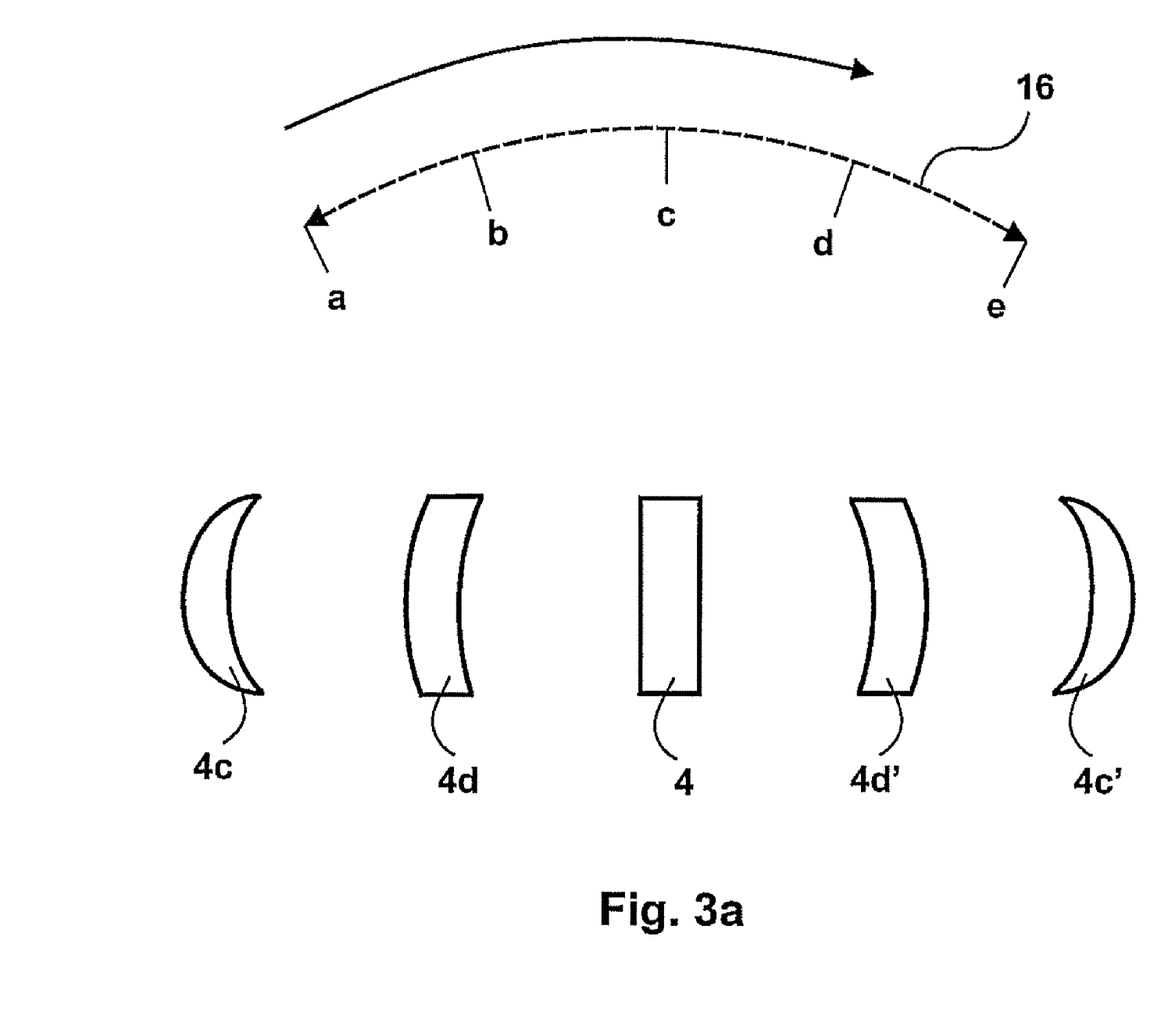
FIG. 3a shows a variety of illuminated-field shapes that the illumination apparatus furnishes in the course of a pivoting motion on a circular-arc-segment carrier.

FIG. 3a shows the progression of the illuminated fields that the spatial light modulator can generate, according to the present invention, in the course of pivoting motion 16. By way of appropriate influence by control unit 6 it is possible, for example, to cause spatial light modulator 3 to generate a crescent-shaped illuminated field 4c at an outermost pivot position a. This crescent-shaped illuminated field 4c transitions, in pivot position b, into an illuminated field 4d that assumes a shape intermediate between a crescent and a rectangle and then becomes, in the central pivot position c, a slit image 4 in the shape of a regular rectangle. Pivot positions d and e then correspond to the mirror-image illuminated fields 4d' and 4c'.

Figure 4:
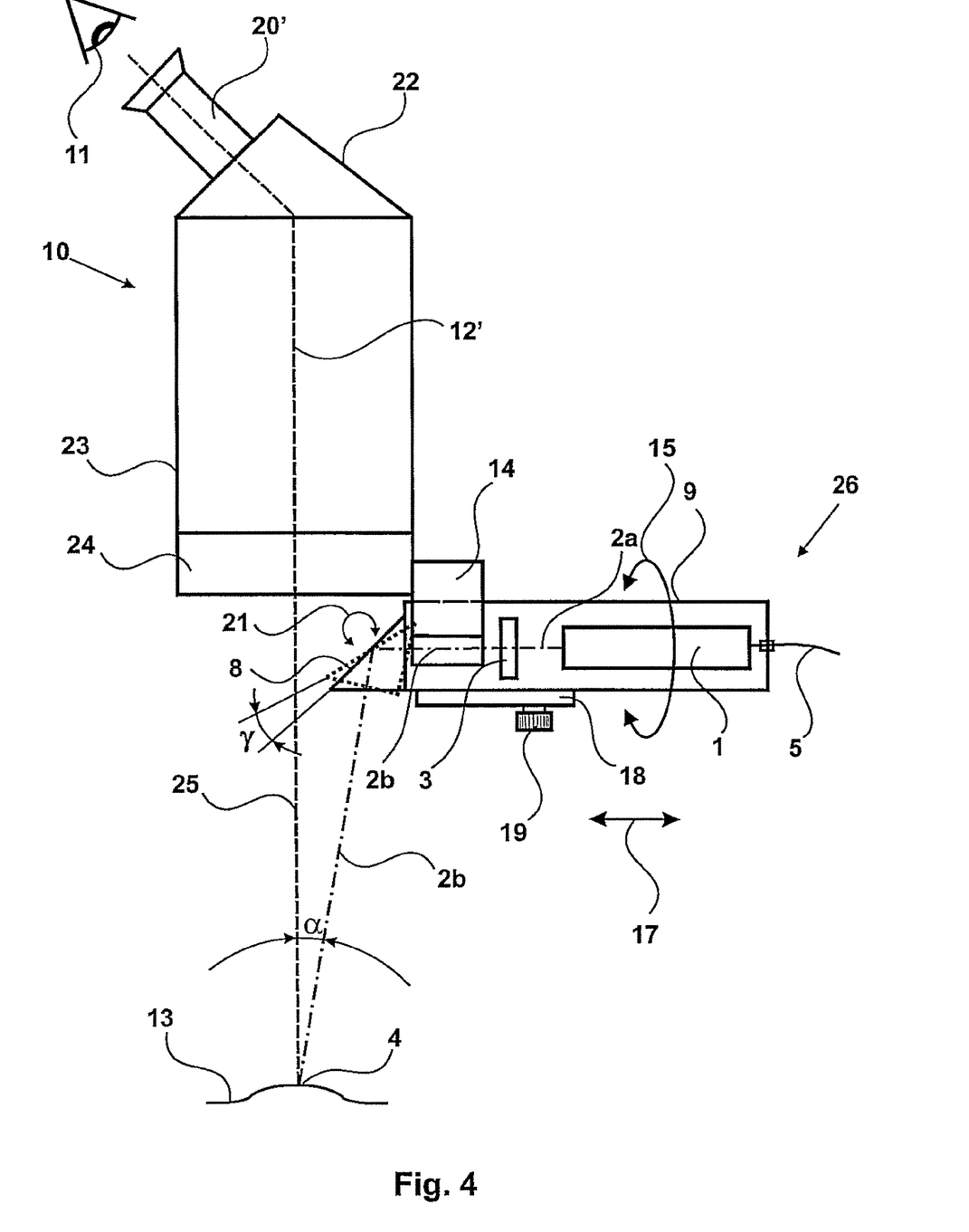
FIG. 4 is a side view of the microscope of FIG. 3.

FIG. 4 is a side view showing the combination of microscope 10 with illumination apparatus 26 of FIG. 3. The beam path having axis 12 is now located behind the one having axis 12'. This view shows that illumination apparatus 26 is accommodated in an illumination housing 9 that is arranged on a circular-arc-segment carrier 14. Illumination apparatus 26 is displaceable along double arrow 17 by means of an apparatus 18 and a mount 19. The illumination angle α constituted by modulated illumination beam path 2b and microscope axis 25 can thereby be varied. In the context of a coaxial illumination, deflecting prism 8 is located between beam paths 12 and 12' (FIG. 3), and microscope axis 25 and the axis of modulated illumination beam path 2b are then coincident. Angles α and β are then equal to zero. When illumination apparatus 26 is shifted, the illumination angle α then changes. To ensure that the modulated illumination beam path represented by axis 2b still enters the pupil of the patient's eye, deflecting prism 8 must be correspondingly tilted by means of an apparatus. Translational motion 17 of illumination axis 26 causes the tilt angle γ to change correspondingly.

Illumination apparatus 26 is mounted on the circular-arc-segment carrier, preferably together with deflecting prism 8, rotatably about axis 2a. The illuminated field on patient's eye 13 can thereby be pivoted or decentered in accordance with rotation 15.

A further variant embodiment (not depicted further) provides for deflecting prism 8 not to participate in rotation 15, so that in addition to the previously mentioned electronically controlled rotation by way of control unit 6, illuminated field 4 on patient's eye 13 can also be mechanically rotated.

PARTS LIST 1, 1a Laser diode
2a Axis of illumination beam path
2b Axis of modulated illumination beam path
3 Spatial light modulator
4 Slit image
4a Central illuminated field
4b Illuminated ring
4c, 4c' Crescent-shaped illuminated field
4d, 4d' Illuminated field transitional between crescent shape and rectangle
5 Electrical supply lead
6 Electronic control unit for 3
7 Electrical supply lead
8 Deflecting prism
9 Deflecting mirror
10 Microscope
11 Observer
12, 12' Beam path
13 Object, patient's eye
14 Circular-arc-segment carrier
15 Rotation about axis 2a
16 Pivoting motion
17 Translational motion
18 Apparatus
19 Mount
20, 20' Eyepiece
21 Tilting motion of 8
22 Tube housing
23 Microscope housing
24 Main objective
25 Microscope axis
26 Illumination apparatus
a-e Pivot position on 16
α, β Illumination angles
γ Tilt angle of 8

What is claimed is:
1. A microscope comprising:
a light source emitting a coherent light beam bundle for travel along a defined illumination beam path; and
a spatial light modulator (SLM) in the illumination beam path for modifying the light beam bundle;

wherein the light source and the SLM are included in an illumination apparatus, and the illumination apparatus further includes an electronic control unit connected to the SLM for electronic activation of the SLM, and wherein the SLM is controlled, by way of the control unit, to vary size and shape of a continuous illuminated field provided by the illumination apparatus over time, and wherein the light source includes two laser diodes emitting light at different wavelengths, the light emitted by the two laser diodes being launched simultaneously onto the illuminated field.

2. The microscope according to claim 1, further comprising means for reflecting light from at least one of the two laser diodes into the illumination beam path such that light from the two laser diodes travels along the illumination beam path.

3. The microscope according to claim 1, further comprising a microscope housing including a circular-arc-segment carrier, wherein the light source and the SLM are included in an illumination apparatus movable along the circular-arc-segment carrier.

4. The microscope according to claim 3, wherein the illumination apparatus further includes an electronic control unit connected to the SLM for electronic activation of the SLM, wherein the control unit controls the SLM such that the illuminated field is a first crescent-shaped illuminated field when the illumination apparatus is at an outermost pivot position (a) on the circular-arc-segment carrier, is a slit-shaped illuminated field when the illumination apparatus is at a central pivot position (c) on the circular-arc-segment carrier, and is a second crescent-shaped illuminated field arranged as a mirror image of the first crescent-shaped illuminated field when the illumination apparatus is at an outermost oppositely located pivot position (e) on the circular-arc-segment carrier.

5. The microscope according to claim 3, wherein an angle of incidence of illumination onto an object, constituting an illumination angle ($\beta$), is variable by moving the illumination apparatus along the circular-arc-segment carrier.

6. The microscope according to claim 1, wherein the light source and the SLM are included in an illumination apparatus, and the illumination apparatus is rotatable about an axis of the illumination beam path.

7. The microscope according to claim 1, wherein the SLM is arranged to change a direction of the light beam bundle.

8. The microscope according to claim 1, wherein the light modulator is controlled, by way of the control unit, to output a slit-shaped illuminated field.

9. The microscope according to claim 1, wherein the light modulator is controlled, by way of the control unit, to output an illuminated field that is centered with respect to an axis of the microscope.

10. The microscope according to claim 1, wherein the light modulator is controlled, by way of the control unit, to output a ring-shaped illuminated field.

11. The microscope according to claim 1, wherein the light modulator is controlled, by way of the control unit, to output a crescent-shaped illuminated field.

12. The microscope according to claim 1, wherein the light modulator is controlled, by way of the control unit, to rotate the illuminated field.

13. The microscope according to claim 1, wherein the light modulator is controlled, by way of the control unit, to provide a continuous transition from one illuminated field shape to another.

14. The microscope according to claim 1, further comprising a microscope housing, wherein the light source and the SLM are included in an illumination apparatus, and the illumination apparatus is displaceable along a longitudinal axis to vary an illumination angle ($\alpha$) at which light is incident to an object.

15. The microscope according to claim 1, wherein the microscope is a surgical stereomicroscope.

16. A method of controlling illumination in a microscope, wherein the microscope comprises (i) a housing including a circular-arc-segment carrier and (ii) an illumination apparatus movable along the circular-arc-segment carrier, the illumination apparatus including a light source emitting a coherent light beam bundle for travel along a defined illumination beam path and a spatial light modulator (SLM) in the illumination beam path for modifying the light beam bundle to define an illuminated field, the method comprising the steps of:
  moving the illumination apparatus along the circular-arc-segment carrier; and
  activating the SLM to change the shape of the illuminated field depending on a location of the illumination apparatus along the circular-arc-segment carrier, wherein the SLM is activated such that the illuminated field has a first crescent shape when the illumination apparatus is at a first outermost pivot position (a) on the circular-arc-segment carrier, the illuminated field has a slit shape when the illumination apparatus is at a central pivot position (c) on the circular-arc-segment carrier, and the illuminated field has a second crescent shape that is a mirror image of the first crescent shape when the illumination apparatus is at a second outermost pivot position (e) on the circular-arc-segment carrier opposite from the first outermost pivot position.

17. A method of controlling illumination in a microscope comprising the steps of:
  activating a light source to emit a coherent light beam bundle travelling along an illumination beam path, the light beam bundle defining a continuous illuminated field; and
  modifying the light beam bundle by controlling a spatial light modulator (SLM) in the illumination beam path to vary size and shape of the continuous illuminated field over time, wherein the light source includes two laser diodes emitting light at different wavelengths, the light emitted by the two laser diodes being launched simultaneously onto the continuous illuminated field.

18. The method according to claim 17, wherein the light beam bundle is modified by controlling the SLM to provide a continuous transition from one illuminated field shape to another.

19. The method according to claim 17, wherein the light beam bundle is modified by controlling the SLM to provide a slit-shaped illuminated field.

20. The method according to claim 17, wherein the light beam bundle is modified by controlling the SLM to provide a continuous illuminated field that is centered with respect to an axis of the microscope.

21. The method according to claim 17, wherein the light beam bundle is modified by controlling the SLM to provide a ring-shaped illuminated field.

22. The method according to claim 17, wherein the light beam bundle is modified by controlling the SLM to provide a crescent-shaped illuminated field.

23. The method according to claim 17, wherein the light beam bundle is modified by controlling the SLM to rotate the illuminated field.

* * * * *